United States Patent
Morris et al.

(10) Patent No.: US 7,123,014 B2
(45) Date of Patent: Oct. 17, 2006

(54) MAGNETIC GRADIENT FIELD PROJECTION

(75) Inventors: Peter Gordon Morris, Wollaton Park (GB); Abdullah Hussien Jamea, Riyadh (SA)

(73) Assignee: BTG International Limited, London (GB)

( * ) Notice: Subject to any disclaimer, the term of this patent is extended or adjusted under 35 U.S.C. 154(b) by 0 days.

(21) Appl. No.: 11/175,125

(22) Filed: Jul. 6, 2005

(65) Prior Publication Data

US 2005/0242815 A1    Nov. 3, 2005

Related U.S. Application Data

(63) Continuation of application No. 10/824,653, filed on Apr. 15, 2004, now abandoned, which is a continuation of application No. 10/188,313, filed on Jul. 3, 2002, now abandoned, which is a continuation of application No. 09/688,737, filed on Oct. 17, 2000, now abandoned, which is a continuation of application No. PCT/GB99/01177, filed on Apr. 16, 1999.

(30) Foreign Application Priority Data

Apr. 17, 1998 (GB) ................... 9808219.1

(51) Int. Cl.
*G01V 3/00* (2006.01)

(52) U.S. Cl. ...................... 324/320; 324/319

(58) Field of Classification Search ............... 324/320, 324/319, 318, 309, 307, 300, 322; 600/410
See application file for complete search history.

(56) References Cited

U.S. PATENT DOCUMENTS

| | | | |
|---|---|---|---|
| 4,276,529 A * | 6/1981 | Heinzerling et al. ........ 335/300 |
| 4,398,150 A | 8/1983 | Barjhoux et al. ............ 324/319 |
| 4,721,914 A * | 1/1988 | Fukushima et al. ......... 324/320 |
| 5,378,989 A | 1/1995 | Barber et al. ............... 324/318 |
| 5,398,989 A * | 3/1995 | Winter et al. .......... 296/203.03 |
| 5,497,089 A * | 3/1996 | Lampman et al. .......... 324/318 |
| 5,677,630 A * | 10/1997 | Laskaris et al. ............ 324/320 |

FOREIGN PATENT DOCUMENTS

| | | |
|---|---|---|
| EP | 0 610 012 A1 | 8/1994 |
| EP | 0 834 747 A2 | 4/1998 |
| EP | 0 834 747 A3 | 3/2000 |
| WO | WO 91/12538 | 8/1991 |
| WO | WO 98/07362 | 2/1998 |

* cited by examiner

*Primary Examiner*—Brij B. Shrivastav
(74) *Attorney, Agent, or Firm*—Nixon & Vanderhye P.C.

(57) ABSTRACT

The projection of magnetic gradient fields useful in Magnetic Resonance Imaging where projection of a gradient outside of a field generating assembly allows imaging of samples which will not physically fit inside the coil confines. The linearity of the projected gradient field is improved by arranging the position of the magnetic field generating coil conductors such that the second derivative of a gradient component is equal to zero. In one practical example the linearity is improved by providing a first circular coil which is positioned so that its center is offset along the axis of the field generating coil assembly by a distance equal to half the radius of the coil. In another example a pair of current carrying wires are selectively positioned offset from a region of interest.

20 Claims, 8 Drawing Sheets

MAGNETIC GRADIENT FIELD PROJECTION

This application is a continuation of application Ser. No. 10/824,653, filed Apr. 15, 2004, now abandoned, which is a continuation of application Ser. No. 10/188,313, filed Jul. 3, 2002, now abandoned, which is a continuation of application Ser. No. 09/688,737, filed Oct. 17, 2000, now abandoned, which is a continuation of PCT/GB99/01177, filed Apr. 16, 1999, the entire content of which is hereby incorporated by reference in this application.

BACKGROUND

1. Technical Field

The present invention relates to the projection of varying magnetic fields, particularly the projection of a substantially linear magnetic gradient field for use in Nuclear Magnetic Resonance Imaging (MRI).

2. Related Art

MRI systems are well-known, and are in commercial use, providing high-quality images in a variety of applications, most notably medical imaging. Typically a sample to be imaged is placed in a strong static magnetic field, for example generated by a superconducting magnet, on which relatively small linearly-varying magnetic fields are imposed. The linearly-varying magnetic field is commonly termed a gradient field, and is used to provide spatial encoding of responsive species within the sample. As is well known, the static magnetic field has field strength of the order of a Tesla, giving rise to a nuclear magnetic resonance frequency of the order of tens or hundreds of megahertz (MHz), the gradient field being much smaller, producing a frequency shift from tens or hundreds of hertz up to a few hundred kilohertz.

Since the basic technology is well-known, it will not be discussed further; reference may be made to Mansfield and Morris "NMR Imaging in Biomedicine", 1982, Academic Press, the subject matter of which is incorporated herein by reference.

A problem with conventional systems, however, is that it is normally necessary for the sample, or at least a substantial proportion thereof, to be enclosed within a magnetic field-generating system. This can be restrictive, particularly where, for example, imaging is required to assist in surgery, as the surgeon's access to the patient may be restricted during imaging.

Some systems have been proposed to overcome these drawbacks. In one known system, a magnet is moveable along a fixed rail. This enables an image of a patient to be taken and then the imaging apparatus can be moved away for the surgeon to operate on the patient. Drawbacks of this arrangement are that it is bulky and cumbersome to operate, and interactive imaging is not possible while the surgeon is operating; surgery must be suspended while imaging is in progress.

Other proposals have included a magnetic field-generating system in which the field-generating arrangement is split into two portions, each portion located on either side of the region of interest (either horizontally or vertically). This allows more access to the region while imaging is being conducted, but the presence of field-generating equipment either side of the region again presents a restriction on access to the patient.

As a further alternative, a system in which a relatively narrow field-generating system is employed has been proposed. This allows access to the region of interest from either side of the field-generating system, but still encloses the sample and therefore again restricts access to the region of interest to a considerable degree.

It would be desirable to provide a system in which a magnetic field-generating system were located substantially at one side of a patient or sample to be imaged. This would allow much greater freedom of access to the region of interest.

U.S. Pat. No. 5,677,630, the disclosure of which is incorporated herein by reference, discloses a magnetic resonance imaging magnet having a superconductive coil assembly in which a sample volume to be imaged can be located on one side of magnetic field-generating system.

However, if the static magnetic field generator of U.S. Pat. No. 5,677,630 were used with conventional gradient field generators to generate a linear field gradient, the problem of restricted access to the sample would still occur because a gradient field generating assembly surrounding the sample would still be necessary; the document does not disclose any practically achievable means for generating the gradients required for imaging.

EP-A-610012 apparently proposes a projected magnetic field for single-sided nuclear magnetic resonance imaging. In this disclosure, however, no details of the arrangements for generating the necessary static and gradient fields are disclosed, and it is believed that, if an attempt were made to put this disclosure into practice, problems owing to the irregular nature of the field and in particular the non-linear gradients expected from the disclosed arrangements would be encountered.

BRIEF SUMMARY

The exemplary embodiment of this invention is concerned specifically with the projection of a varying (or gradient) field. This may be used, for example, in conjunction with a system for projecting a static magnetic field to provide a complete NMR imaging apparatus, with which the invention is particularly concerned. The invention is, however, more generally applicable to projection of a gradient field and may find application in other imaging or testing where a linearly varying magnetic field is required, or in the projection of a radio frequency field such as is used in rotating frame Zeugmatography type experiments. Zeugmatography is described by Hoult in Journal of Magnetic Resonance 33 183 (1979), the subject matter of which is incorporated herein by reference.

In a first aspect, the invention provides apparatus for generating a magnetic field gradient component, comprising magnetic field-generating means arranged to generate, in use, said gradient component which is substantially linear within a defined sample volume offset from and outside said apparatus.

Thus, in contrast to conventional practice in which centro-symmetric double-sided field-generating arrangements have been employed in order to generate a linearly varying field within a coil assembly, the inventor has found that a substantially linearly varying field can be projected over a useful sample volume offset from and outside the field-generating means. By "outside" in this specification, we mean that the components of the field-generating means do not enclose the sample volume (as is the case in a conventional Maxwell pair arrangement). By "sample volume" in this specification, we mean a defined spatial region in which a sample to be tested or imaged is intended to be located; this will usually be associated with means for projecting a substantially homogeneous static field, means for maintaining desired position of the sample and means for transmitting and receiving radio frequency signals. The defined sample volume need not occupy the entire physical volume available to receive a sample; typically the apparatus will accommodate a larger sample than can effectively or accurately be imaged.

Preferably the field generating components are located to one side of a plane through the sample volume; this enables the sample to be accessed from an entire hemisphere the other side of said plane. However, in certain circumstances, one or more modifying components may be provided on the other side of said plane (for example to improve gradient linearity), provided the modifying components are small in comparison to the field generating elements and do not substantially impede access to the sample volume; it is preferred not to include such components.

By substantially linear, we mean that preferably, any error in results due to variation in the value of the gradient is of the same order of magnitude as, and preferably less than any error due to other sources of experimental error.

Preferably said gradient component corresponds to variation in the a component of the magnetic field produced by said magnetic field generating means along a predetermined direction.

Preferably, the second derivative of said component of the magnetic field, with respect to distance along said predetermined direction is substantially equal to zero at least about a predetermined point within the defined sample volume, preferably at or adjacent the centre of the sample volume.

By substantially zero, we mean that the magnitude of the relevant derivative is within the limits of experimental accuracy of measurement. By "about a predetermined point", we mean that the derivative may be exactly zero at at least one point and should remain close to zero over over a finite range around that point, preferably throughout the sample volume.

Preferably also, the third derivative of said component of the magnetic field with respect to distance along said predetermined direction is substantially equal to zero at least about said predetermined point within the defined sample volume.

Preferably, the deviation of said gradient component from a given constant value is less than about 10%, preferably less than 5%, 2%, 1%, 0.5% or 0.1% along the length of a given line passing through the sample volume.

Preferably, the magnetic field-generating means comprises a plurality of field generating elements arranged so that the variation of a component of the resultant magnetic field generated by said elements with distance along a predetermined direction corresponding to said magnetic field gradient component is substantially linear within the defined sample volume; the combined effect of several elements may give a more uniform gradient than if a single element is employed.

The apparatus may have further magnetic field-generating cans arranged to generate, in use, a further gradient component which is substantially linear within a defined sample volume offset from and outside said assembly, said further gradient component being substantially orthogonal to said gradient component; this may enable 2 or 3 dimensional imaging. The magnetic field-generating means and said further magnetic field-generating means are preferably independently controllable.

One gradient component may be an axial component, along a direction projecting away from the apparatus and another gradient component is a transverse component, along a direction substantially perpendicular to the axial component; this enables effective 2-dimensional imaging. In such a case said magnetic field-generating means and said further magnetic field-generating means having mutually dissimilar configurations.

Alternatively, both gradient components may-be transverse components, generated by similar elements.

Advantageously, the apparatus includes a third magnetic field-generating means arranged to generate, in use, a third gradient component which is substantially linear within a defined sample volume offset from and outside said assembly, said third gradient component being substantially orthogonal to said gradient component and said further gradient component.

The apparatus is advantageously mounted within a housing, the defined sample volume being positioned outside said housing.

The apparatus may include means for establishing a desired relative position between a sample and said housing; this may entail supporting a sample, such as a patient, on the housing, or vice-versa. This enables repeatable experiments to be performed. The establishing means may comprise a support surface defined by the housing on which a sample can be positioned.

The apparatus is most advantageously arranged for use in magnetic resonance imaging, wherein the defined sample volume corresponds to a volume of a sample to be imaged, said volume being associated with means for generating a static magnetic field therein and means for transmitting or receiving radio frequency signals, and may further include at least one of said means for generating a static magnetic field and said means for transmitting or receiving radio frequency signals mounted within said housing.

The means for generating a static magnetic field preferably comprises a plurality of magnetic elements, preferably superconducting coils, mounted within the housing. This may ensure access to the sample volume is substantially unimpeded by static magnetic field generating elements and magnetic gradient generating elements over a hemisphere.

Advantageously, the means for transmitting or receiving radio frequency signals comprises a butterfly coil mounted with the plane thereof substantially parallel to and adjacent a surface of the housing facing said sample volume. In this case the coil is physically parallel to the imaging plane, and generates an rf field which is parallel to the imaging plane and hence orthogonal to the static field in the axial direction. This arrangement therefore provides a compact transmitter/receiver which may be located close to the sample.

In a preferred embodiment, arranged to generate a substantially linear axial gradient component, the magnetic field-generating means comprises a substantially circular coil positioned so that the centre of the coil is displaced along the axis of the coil from the centre of the sample volume by a distance approximately equal to half of the radius $r_1$ of the coil; this is convenient, yet effective. This arrangement gives a substantially zero second order term. In the ideal case, where the coil is perfectly circular and of negligible cross section, the second order term is identically equal to zero at the central sample point.

Preferably, the magnetic field-generating means includes a further coil, the axis of the further coil being substantially coincident with the axis of said coil, the distance of said further coil from the centre of the sample volume being substantially equal to half of the radius $r_2$ of the further coil, the coils being connected so that, in use, the relation $$\left(\frac{r_2}{r_1}\right)^4 = -\frac{I_2 N_2}{I_1 N_1}$$

is substantially satisfied where $I_1$ and $I_2$ are the currents flowing through said coil and said further coil respectively, and $N_1$ and $N_2$ are the numbers of turns of said coil and said further coil respectively, the radii of the coils being mutually different, the currents in the coils flowing in opposite directions; this is found to give greatly improved linearity; this arrangement can provide a substantially zero third order derivative.

Further coils (or other field generating elements) may be provided to cancel out higher order derivatives. Thus, the magnetic field-generating means may comprise a plurality of substantially circular coils of differing radii arranged in substantially parallel planes with their centres passing through a common axis.

As an alternative to a plurality of discrete coils, a substantially continuous field generating assembly may be employed, for example, wound on a conical former. This may allow more accurate tailoring of the gradient field, and a higher gradient power to be achieved. With a substantially continuous winding, preferably the density of winding varies to vary the effective current density at different positions; this enables a desired current density profile to be achieved without requiring complex connection to the coil(s) and adjustment of current. Of course, there may be discontinuities, particularly where the direction of winding reverses. In one implementation, two windings may be provided, connected in opposite directions, the winding densities of the two windings differing.

In another preferred embodiment, arranged to generate a substantially linear transverse field gradient, the magnetic field-generating means, comprises two substantially parallel long substantially straight conductors substantially symmetrically located about an axis passing through the centre of the sample volume, the conductors being connected to carry substantially equal currents in a common direction and lying in a plane substantially perpendicular to the field axis and offset from the centre of the sample volume; this is again convenient yet effective.

By "long" is meant that the length of the wires is sufficient so that any distortion caused by the ends of wires (or the fact that the wires are of finite length) is small in comparison to the limits of accuracy of the system. Typically, this requires the length of the wires to be at least double the spacing of the wires, and preferably at least double the length of the effective sample volume.

Preferably, the spacing $a_1$ between the conductors and the distance $d_1$ of the plane through the conductors from a predetermined point within the sample volume, preferably the centre of the sample volume, substantially satisfy the relation $a_1^2 = 4d_1^2(3+/-2\sqrt{2})$; this improves linearity.

Most preferably, a further pair of substantially parallel conductors is provided, the plane of the further pair being substantially parallel to the plane of said pair of conductors, the current in the further pair arranged to flow in the opposite direction to the current in said pair of wires, the distance of the further pair being greater than the distance of said pair of wires, the separation $a_2$ of the further pair of conductors or wire bundles and the distance $d_2$ of the further pair of conductors or wire bundles from the sample plane substantially satisfying the relation $a_2^2 = 4d_2^2(3+/-2\sqrt{2})$, the currents in the conductors or wire bundles further substantially satisfying the relation $\Sigma I_2/\Sigma I_1 = -(a_2/a_1)^3$, where $\Sigma I_1$, $\Sigma I_2$ are the total currents (equal to the product NI in each case for wire bundles, or just 1 for a single conductor) in each conductor for the first and second pairs respectively; this can provide greatly improved linearity, with respect to both the transverse and the axial direction.

Alternatively, if very high transverse linearity is desired, at the expense of some linearity in the z direction (for example for imaging thin samples), the relation $\Sigma I^2/\Sigma I_1 = -(a_2/a_1)^6$ should be satisfied instead of $\Sigma I_2/\Sigma I_1 = -(a_2/a_1)^3$; this can provide 5th order linearity.

As with the axial gradient arrangement further field generating elements may be included to improve linearity further. In place of discrete field generating assemblies, a substantially continuous arrangement may be provided, for example bundles of parallel wires distributed over a defined surface, the density of wires being adjusted to generate a desired current density profile.

The magnetic field generating means may comprise an extended substantially continuous arrangement of current carrying elements, the current density throughout the arrangement conforming substantially to a predetermined profile.

The apparatus preferably further comprises means for applying current to generate desired gradient components in accordance with a given imaging protocol.

The apparatus is preferably arranged to control magnetic field generating means arranged to generate an axial gradient component to effect frequency encoding or slice selection, but not phase encoding; this enables the offset in a typical axial gradient arrangement to be accommodated.

As an additional application, the apparatus may be for use in magnetic resonance spectroscopy or in zeugmatography.

As an alternative to gradient projection, the field may be a time-varying component of a radio-frequency signal, the apparatus being arranged to generate a linearly varying radio-frequency field for use in NQR testing of a sample within the sample volume.

Whilst NMR systems, which use static magnetic fields and NQR systems which use radio frequency excitation are in general quite distinct, the inventor has appreciated that, as an additional application, the field generating assemblies proposed may also be applicable to projection of a linearly varying radio frequency field, as may be useful in NQR experiments, for example imaging based on rotating frame zeumatography (see the above Hoult reference).

In a further aspect, the invention provides apparatus for generating a radio frequency field for use in NQR testing of a sample comprising field-generating means arranged to generate, in use, said field which varies substantially linearly in intensity within a defined sample volume offset from and outside said apparatus.

In a preferred embodiment, the invention provides apparatus for generating at least one magnetic gradient component for use in magnetic resonance imaging of a sample, the apparatus comprising:
  a housing;
  a defined sample volume outside the housing;
  magnetic field generating elements located within the housing, the resultant field from the elements varying substantially linearly with distance along at least one predetermined direction, said at least one predetermined direction corresponding to said at least one gradient component, throughout the defined sample volume.

This may further include:
a magnet assembly within the housing for generating a static magnetic field within the defined sample volume;
a radio frequency transceiver within the housing for transmitting signals to and receiving signals from the defined sample volume;
control apparatus for controlling said magnetic field generating elements to generate said at least one gradient component in conformity with an imaging protocol.

Preferably an upper surface of the housing comprises an operating surface over which a sample to be imaged, preferably a patient, can be positioned.

The invention also provides, in a first method aspect, a method of generating a magnetic field gradient component within a sample, comprising positioning the sample outside and offset from magnetic field generating means and arranging the magnetic field generating means to produce said gradient component which is substantially linear within a defined sample volume within at least a portion of the sample.

Arranging may include providing field generating elements having predetermined positions with respect to the sample volume. Additionally or alternatively, arranging may include controlling the current(s) supplied to the field generating elements to generate a desired gradient.

In a second method aspect, the invention provides a method of configuring a magnetic field-generating assembly to produce a substantially linear magnetic field gradient component within a defined sample volume offset from and outside the assembly, comprising arranging the assembly with respect to the sample volume so that the second derivative of a desired component of the magnetic-field with respect to distance along a predetermined direction corresponding to said magnetic field gradient component is substantially equal to zero at least about a predetermined point within the defined sample volume, preferably at or adjacent the centre of the sample volume.

Preferred features of the first apparatus aspect can be applied to the other apparatus aspects and to the method aspects, unless otherwise stated, and vice versa.

BRIEF DESCRIPTION OF THE DRAWINGS

An embodiment of the invention will now be described, by way of example, with reference to the accompanying drawings in which:

FIG. 13 show measured profiles of the phantoms shown in FIG. 12a;

DETAILED DESCRIPTION OF EXEMPLARY EMBODIMENTS

We begin with a theoretical discussion of the production of magnetic field gradients by certain elements.

In MRI, to be able to assign a signal as being derived from a particular spatial region, it is usual to apply linear magnetic field variations in addition to the main magnetic field $B_0$. This is normally achieved using gradient coils to produce the linear field variations in each of the three orthogonal directions. As mentioned above, a number of conventional designs exist, which employ elements surrounding the sample. Here we consider asymmetric arrangements. Somewhat unexpectedly, we find that substantially linear gradients can be obtained from asymmetric coil arrangements if certain conditions are observed; the theory presented below can be extended to other coil elements.

It is usual in MRI to use three gradient coils to generate the magnetic field gradient in the three principal directions, $G_x$=$dB_z/dx$, $G_y$=$dB_z/dy$, $G_z$=$dB_z/dz$, which enables the complete MRI repertoire of slice selection, frequency and phase encoding. For consistency we shall assign the z-direction always to be defined as the direction of the main magnetic field $B_0$. Normally, windings for $G_y$ are obtained by rotating the pattern of the windings for $G_x$ by 90°. Gradient coils, therefore, consist of two kinds of gradient sets: a longitudinal magnetic field gradient set to produce a linear magnetic field gradient $G_z$ parallel to the main magnetic field $B_0$ and a transverse magnetic field gradient set to produce linear magnetic field gradients $G_x$ and $G_y$ in the plane orthogonal to $B_0$. These are considered separately below.

Transverse Field Gradient.

Figure 1:
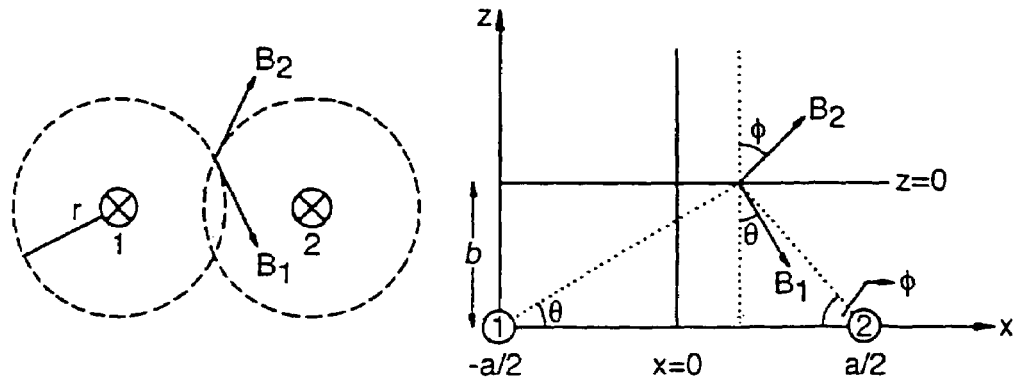
FIG. 1 shows schematically the magnetic field around two parallel wires separated by a distance a carrying a current I (into the paper)

According to the Biot-Savart expression an infinitely long straight conductor with negligible cross section carrying a current I generates a magnetic field B in a direction perpendicular to the conductor (FIG. 1). The magnitude of B at a point in space at a perpendicular distance r from the conductor is given by $$B = \frac{\mu_0 I}{2\pi r} \tag{1}$$

where $\mu_0$ is the permeability of free-space ($=4\pi\times10^{-7}$). The vector B lies in the plane orthogonal to I and is perpendicular to r. The orientation of B follows the right-hand rule.

For a bundle consisting of N wires, B will scale up linearly and is given by $$B = \frac{\mu_0 I N}{2\pi r} \quad (2)$$

It will be appreciated that a single conductor carrying a current I may conveniently be replaced by a bundle of N smaller conductors each carrying a current i, where I=Ni. Throughout this specification, which term includes the claims, references to a "conductor", unless otherwise stated, are intended to encompass a composite "conductor" comprising a plurality of wire elements or the like. The currents in wires in a bundle need not all be equal (although for practical reasons, the elements in a bundle will normally be wired in series to provide a more convenient load for a conventional gradient driver circuit, adapted for driving a multi-turn coil), in which case the current in the composite conductor formed by the bundles must be calculated as the sum of the currents in each element.

Figure 3:
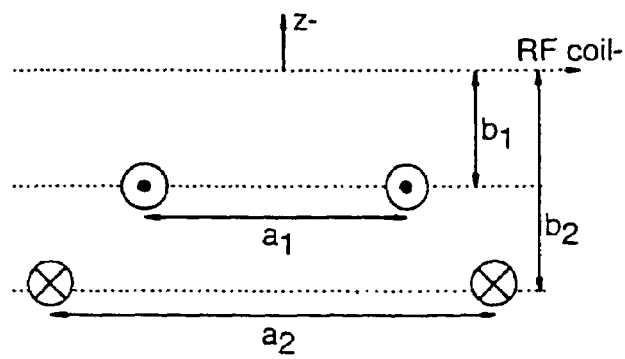
FIG. 3 shows a modified arrangement of FIG. 1 employing a second pair of conductors or wire bundles.

It is proposed to use two parallel wire bundles separated by a distance a carrying a current I in the same direction, the two bundles lying in the plane orthogonal to the z-direction as shown in FIG. 3. The z component of the magnetic field from wire bundle 1 at a point a normal distance b above the plane containing the two wire bundles will be given by $$B_{z1} = \frac{\mu_0 N I}{2\pi\left[b^2 + \left(x+\frac{a}{2}\right)^2\right]^{\frac{1}{2}}}(-\cos\theta) \quad (3)$$

$$B_{z1} = \frac{-\mu_0 N I\left(x+\frac{a}{2}\right)}{2\pi\left[b^2 + \left(x+\frac{a}{2}\right)^2\right]} \quad (4)$$

and, similarly, the z component of the magnetic field from wire bundle 2 is given by $$B_{z2} = \frac{\mu_0 N I}{2\pi\left[b^2 + \left(\frac{a}{2}-x\right)^2\right]^{\frac{1}{2}}}(\cos\phi) \quad (5)$$

$$B_{z2} = \frac{-\mu_0 N I\left(\frac{a}{2}-x\right)}{2\pi\left[b^2 + \left(\frac{a}{2}-x\right)^2\right]} \quad (6)$$

The field resulting from the pair arrangement of wire bundles along the plane a normal distance b above the wire (defined as the plane z=0) will therefore be $$B_z(x) = \frac{\mu_0 N I}{\pi}\left[\frac{a-2x}{4b^2+(a-2x)^2} - \frac{a+2x}{4b^2+(a+2x)^2}\right] \quad (7)$$

As expected from symmetry conditions $B_z(x)=0$ for x=0. The Taylor expansion of $B_z$ about x=0 (the zero field point) gives the theoretical field in its component orders as:

$$B_z(x) = B_z(0) + \frac{(x)}{1!}\frac{\delta B_z(0)}{\delta x} + \frac{(x)^2}{2!}\frac{\delta^2 B_z(0)}{\delta x^2} + \quad (8)$$
$$\frac{(x)^3}{3!}\frac{\delta^3 B_z(0)}{\delta x^3} + \frac{(x)^4}{4!}\frac{\delta^4 B_z(0)}{\delta x^4} + \frac{(x)^5}{5!}\frac{\delta^5 B_z(0)}{\delta x^5} + \ldots$$

The first term in this expression denotes the steady state field of the system (zero), the second term is the desired linear field gradient, and the other terms are successively higher order non-linear components of the field. Differentiating equation (7) we obtain:

$$\frac{\delta B_z}{\delta x} = \frac{2\mu_0 N I}{\pi}\left[\frac{(a-2x)^2-4b^2}{(4b^2+(a-2x)^2)^2} - \frac{(a+2x)^2-4b^2}{(4b^2+(a+2x)^2)^2}\right] \quad (9)$$

At x=0 this gives a linear field gradient $$\frac{\delta B_z}{\delta x} = \frac{4 N I \mu_0}{\pi}\left[\frac{a^2-4b^2}{(a^2+4b^2)^2}\right] \quad (10)$$

For gradient linearity, the higher order components must be eliminated.

It so happens that, due to symmetry, at x=0, the 2nd and 4th order components (and all higher even orders) are identically zero.

Thus, a pair of wire bundles gives a substantially linear gradient above the plane of the wires to third order in x; this basic arrangement can be used to project a desired gradient field.

We have found that gradient linearity can be improved further.

At x=0, the 3rd order component reduces to $$\frac{\delta^3}{\delta x^3}B_z(x)_{x=0} = \frac{96\mu_0 I N}{\pi}\left[\frac{a^4-24b^2 a^2+16b^4}{(a^2+4b^2)^4}\right] \quad (11)$$

We have found that this non-zero component can be made to vanish if we choose:

$$a = 2b(1\pm\sqrt{2}) \quad (12)$$

This is the condition for which the system is linear up to fifth order.

Thus a pair of bundles substantially satisfying equation (12) can be used to project a gradient which is substantially linear to fifth order in x.

If the larger value of a in equation (12) is substituted in equation (10), since it will maximise the region in which the gradient is linear, the field gradient can be written as:

$$\frac{\delta B_z}{\delta x} = \frac{N\mu_0 I}{\pi a^2}\frac{(4+3\sqrt{2})}{(2+\sqrt{2})} \quad (13)$$

Using equations (12) and (13) a linear field gradient of a desired strength can be set by selecting N, I, and a.

FIG. 2 show a plots of the theoretical field $B_z(x)$ (FIG. 2a), the gradient $dB_z(x)/dx$ (FIG. 2b), and the derivatives up to the fourth order (FIGS. 2c–2e) for a chosen value of a of 2.4 cm in the plane z=0 (see FIG. 1). As expected $B_z$ is linear and $dB_z(x)/dx$ is constant in the region near x=0. The second, third and fourth orders derivatives vanish at x=0 as expected, and remain small over an extended region about x=0 (broken lines drawn at x=0.3 cm and x=0.3 cm).

Thus, contrary to expectations, it is possible to project a highly linear gradient using a single pair of wires offset from the centre of the sample, the linearity being improved by selecting the spacing of the wires and the imaging plane appropriately.

To improve linearity still further, we have proposed to introduce a second pair of bundles, as shown in FIG. 3. The resultant field from the double pair arrangement is simply the sum of the fields produced by each pair of bundles and is given by:

$$B_z(x) = \frac{\mu_0 N_1 I_1}{\pi}\left[\frac{a_1 - 2x}{4b_1^2 + (a_1 - 2x)^2} - \frac{a_1 + 2x}{4b_1^2 + (a_1 + 2x)^2}\right] + \frac{\mu_0 N_2 I_2}{\pi}\left[\frac{a_2 - 2x}{4b_2^2 + (a_2 - 2x)^2} - \frac{a_2 + 2x}{4b_2^2 + (a_2 + 2x)^2}\right] \quad (14)$$

where $N_2$, $I_2$, $a_2$ and $b_2$ are the number of turns, current, separation of the current bundles and distance from the central imaging plane for the second pair arrangement respectively.

At x=0 the fifth order derivative can be written as:

$$\left(\frac{\delta^5 B_z(x)}{\delta x^5}\right)_{x=0} = \frac{\mu_0 N_1 I_1}{\pi}\left[\frac{a_1^6 - 60 a_1^4 b_1^2 + 240 b_1^4 a_1^2 - 64 b_1^6}{(a_1^2 + 4b_1^2)^6}\right] + \frac{\mu_0 N_2 I_2}{\pi}\left[\frac{a_2^6 - 60 a_2^4 b_2^2 + 240 b_2^4 a_2^2 - 64 b_2^6}{(a_2^2 + 4b_2^2)^6}\right] \quad (15)$$

We have found that this term vanishes if:

$$\left(\frac{a_2}{a_1}\right)^6 = -\frac{N_2 I_2}{N_1 I_1} \quad (16)$$

The ratios $a_2/a_1$ and $N_2 I_2/N_1 I_1$ can be manipulated to make the transverse field gradient linear up to the seventh order by satisfying the above condition. The minus sign in equation (16) indicates that the current in the second pair of bundles must be flowing in the opposite direction with respect to the first pair.

Thus by employing two pairs of wires substantially satisfying equations (12) and (16), a very high degree of linearity can be achieved in an image plane offset from the wires.

Figure 4A:
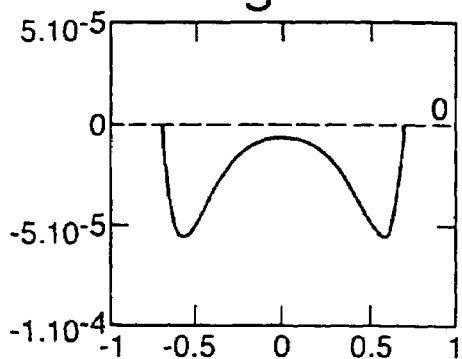
FIG. 4 show a comparison of the 5th order derivatives for (a) the arrangement of FIG. 1 and (b) the arrangement of FIG. 3, in which $a_1$=2.4 cm, $a_2$=2.72 cm and $N_2I_2/N_1I_1$=−2.
Figure 4B:
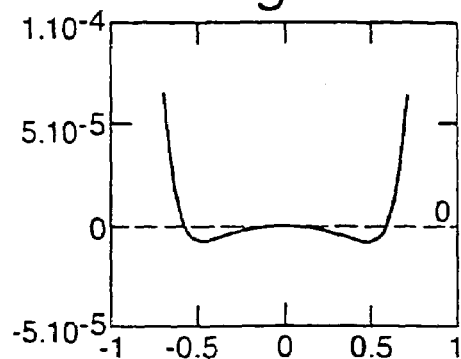
Figure 2A:
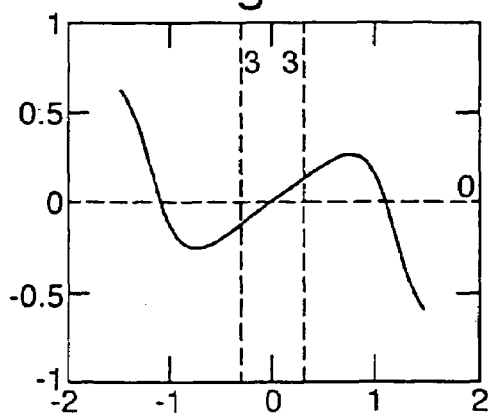
FIG. 2 show, for a value of a=2.4, plots of (a) the field, (b) the gradient, (c) the 2nd derivative (d) the third derivative, and (e) the 4th derivative of the field produced by the arrangement of FIG. 1.
Figure 2B:
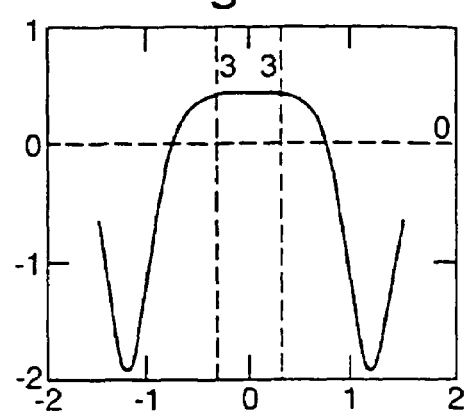
Figure 2C:
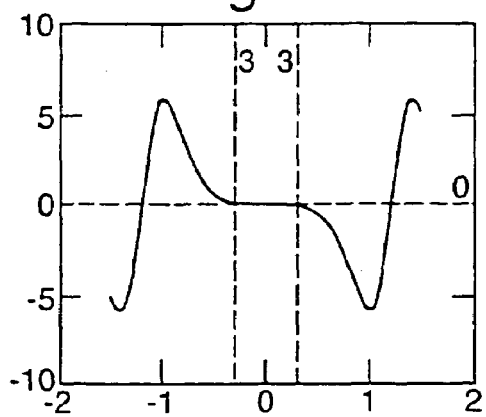
Figure 2D:
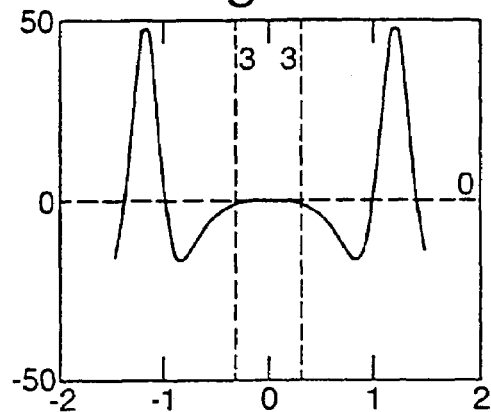
Figure 2E:
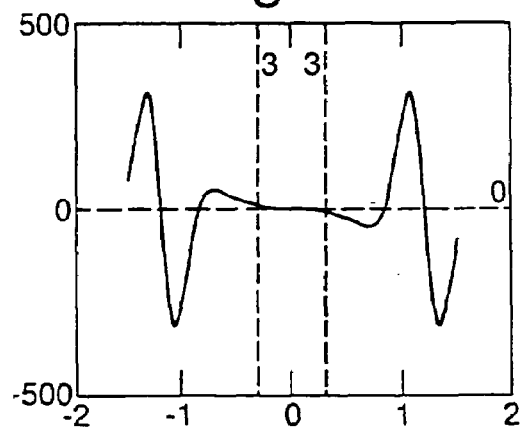

FIG. 4 show the theoretical field plot of the fifth order derivative for a single pair design (FIG. 4a) and double pair design (FIG. 4b) for values chosen to satisfying the above condition (16).

The previous analysis considered only the variation in the x-direction (i.e. within the plane z=0) and ignored variation of the field in the z-direction (z≠0). In practice the linearity of the field was found to decrease outside the z=0 plane.

We have found that an alternative double pair arrangement can advantageously be used to alleviate this; instead of removing the fifth order term, the second pair can be used to reduce the variation in the z direction.

The field resulting from the double pair arrangement in the z=0 plane is given in equation (14). The z-dependence is explicitly recognised in the two-dimensional field expression:

$$B_z(x, z) = \quad (17)$$
$$\frac{\mu_0 N_1 I_1}{\pi}\left[\frac{a_1 - 2x}{4(b_1 + z)^2 + (a_1 - 2x)^2} - \frac{a_1 + 2x}{4(b_1 + z)^2 + (a_1 + 2x)^2}\right] +$$
$$\frac{\mu_0 N_2 I_2}{\pi}\left[\frac{a_2 - 2x}{4(b_2 + z)^2 + (a_2 - 2x)^2} - \frac{a_2 + 2x}{4(b_2 + z)^2 + (a_2 + 2x)^2}\right]$$

Using this expression, it can be shown that the linear variation of the gradient in the z direction $$\left(\frac{d}{dz}\frac{dB_z(x, z)}{dx} = \frac{d^2 B_z(x, z)}{dz dx}\right)$$

at x=0, z=0, can be made to vanish by setting $$\left(\frac{a_2}{a_1}\right)^3 = -\frac{N_2 I_2}{N_1 I_1} \quad (18)$$

Again the minus sign in the above condition shows that the current in the second pair of bundles must be flowing in the opposite direction with respect to the first pair. Therefore, by manipulating either the current or the number of turns in the second pair of bundles to meet the condition in equation (18), the linear variation of field gradient in z direction can be substantially eliminated.

Thus, by using two pairs of wires substantially satisfying equations (12) and (18), a highly linear gradient can be projected with minimal variation in the z direction; this is useful for extending the thickness of the sample volume without having to re-configure the apparatus.

Figure 5A:
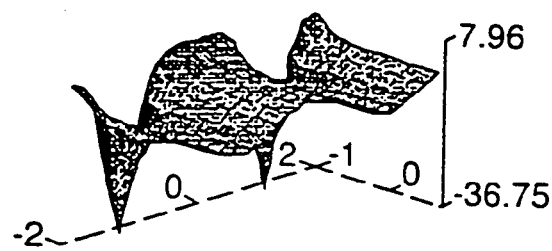
FIG. 5 show surface plots of the field gradients for various coil arrangements.
Figure 5B:
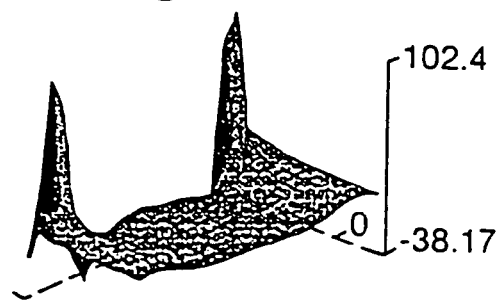
Figure 5C:
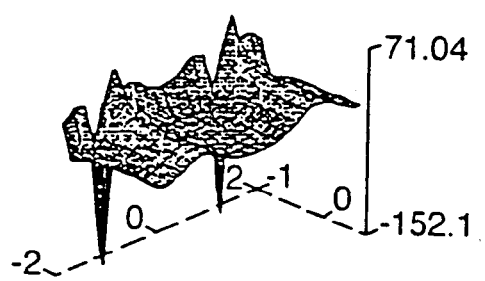
Figure 5D:
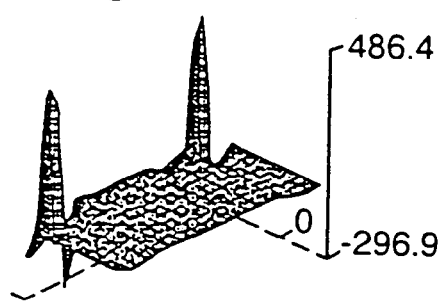

FIGS. 5a and 5b show surface plots of the field gradient, $$\left(\frac{dB_z(x, z)}{dx}\right)$$

for the single and double pair arrangements respectively and FIGS. 5c and 5d show surface plots of and the gradient's derivative with respect to z, $$\left(\frac{d^2 B_z(x, z)}{dz dx}\right),$$

for the single and double pair arrangements respectively. In both cases $a_1$ is chosen as 2.4 cm. For the double pair $a_2$ is chosen to be 3 cm to satisfy the condition in equation (18) for $N_2 I_2/N_1 I_1 = -(3/2.4)^3 \approx -2$.

It can be seen clearly from the plots in FIG. 5 that the gradient linearity in the z-direction is vastly improved in the double pair arrangement.

To discuss the field variation in two dimensions more carefully the Taylor expansion of the field $B_z(x,z)$ in two dimension must be considered. The Taylor expansion in two variables x, z is given by:

$$B(x, z) = B(0, 0) + \frac{x}{1!}\frac{\delta B(0, 0)}{\delta x} + \frac{z}{1!}\frac{\delta B(0, 0)}{\delta z} + \qquad (19)$$
$$\frac{1}{2!}\left(x^2\frac{\delta^2 B(0, 0)}{\delta x^2} + 2xz\frac{\delta^2 B(0, 0)}{\delta x \delta z} + z^2\frac{\delta^2 B(0, 0)}{\delta z^2}\right) +$$
$$\left(x^3\frac{\delta^3 B(0, 0)}{\delta x^3} + 3x^2 z\frac{\delta^3 B(0, 0)}{\delta x^2 \delta z} + 3xz^2\frac{\delta^3 B(0, 0)}{\delta x \delta z^2} + z^3\frac{\delta^3 B(0, 0)}{\delta z^3}\right)$$

For second order terms, at x=0, z=0, the term $$\frac{d^2 B_z}{dz^2}$$

is found to be zero, the term $$\frac{d^2 B_z}{dx^2}$$

is also zero as expected from symmetry consideration, and we have seen that the condition given in equation (18) eliminates the non-zero second order term, $$\frac{d^2 B_z}{dxdz}.$$

For third order terms, again the terms $$\frac{d^3 B_z(x, z)}{dx^2 dz} \text{ and } \frac{d^3 B_z(x, z)}{dz^3}$$

are found to be zero at x=0, z=0, and we have seen that $$\frac{d^3 B_z(x, z)}{dx^3}$$

vanishes under the conditions given in equation (12). We are left with the non-zero term $$\frac{d^3 B_z(x, z)}{dxdz^2}$$

which we have found cannot be made to vanish unless $$\frac{a_2}{a_1} = 1.$$

Unfortunately, this represents the trivial solution, having the double pair of bundles coincident, with currents flowing in opposite directions, generating zero field.

This means that the transverse gradient is linear only up to the third order in the z direction.

The arrangements described above enable a substantially linear transverse gradient to be projected, so can be used for the Gx and Gy "coils" of a practical instrument in which the sample volume is offset from the gradient projection assembly.

The above arrangement cannot readily be employed to project an axial gradient; a different arrangement suitable for this purpose will now be described.

In the above discussion, reference has been made to infinitely long conductors or wire bundles. In practice, of course, the conductors are of finite length. Provided the conductors return substantially parallel to the field component, any return portions of the wire will not affect the field. If the bundles are in fact formed as rectangular coils, the distant portion of the coil should be sufficiently far from the sample to prevent interference with the sample. There will still be some effect due to the finite length of the conductors, particularly closer to the ends of the conductors. As will be explained below, in practical implementations, this does not cause significant problems, and can to some extent, be compensated.

The length of the conductors should be greater than the conductor spacing, preferably at least twice the length of the active sample volume, and ideally twice the conductor spacing. The length of the conductors is preferably sufficient to ensure that non-linearities attributable to the finite size of the elements are of the same order of magnitude as other non-linearities; this can be determined empirically for a given set up.

Longitudinal Field Gradient.

We proposed using a substantially circular coil as the basic element. A circular coil of radius r, of N turns, carrying a current I produces a magnetic field at a distance z from its centre given by $$B_z = \frac{\mu_0 N I r^2}{2(r^2 + z^2)^{\frac{3}{2}}} \qquad (20)$$

Figure 6:
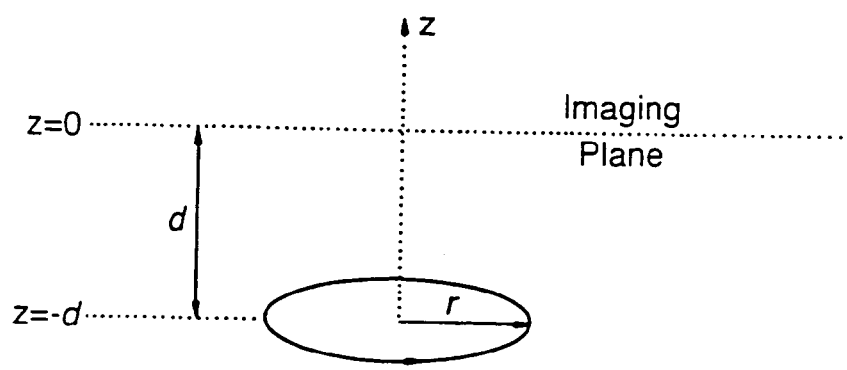
FIG. 6 shows a diagram of a coil consisting of a single loop element of radius r.

With the coil geometry shown in FIG. 6, the direction of B is perpendicular to the coil plane, i.e. along the z direction. It is possible to expand about a point z=0 at a perpendicular distance d from the centre of the coil using a Taylor expansion such that $$B_z(z) = B_z(0) + \frac{(z)}{1!}\frac{\delta B_z(0)}{\delta z} + \frac{(z)^2}{2!}\frac{\delta^2 B_z(0)}{\delta z^2} + \frac{(z)^3}{3!}\frac{\delta^3 B_z(0)}{\delta z^3} + \qquad (21)$$

This will give a linear gradient if all the terms higher than the first order term vanish. The first order differential is $$\frac{\delta B_z}{\delta z}(z) = -\frac{3\mu_0 N I r^2 (d+z)}{2(r^2 + (d+z)^2)^{\frac{5}{2}}} \qquad (22)$$

The second order differential is $$\frac{\delta^2 B_z}{\delta_z^2}(z) = -\frac{3\mu_0 N I_r^2 (r^2 - 4(d+z)^2)}{2(r^2 + (d+z)^2)^{\frac{7}{2}}} \quad (23)$$

At z=0 this term is found to vanish if $$d = \frac{r}{2} \quad (24)$$

Thus, a substantially circular coil can indeed be used to project a substantially linear gradient, up to third order in z, if equation (24) is satisfied.

Figure 7:
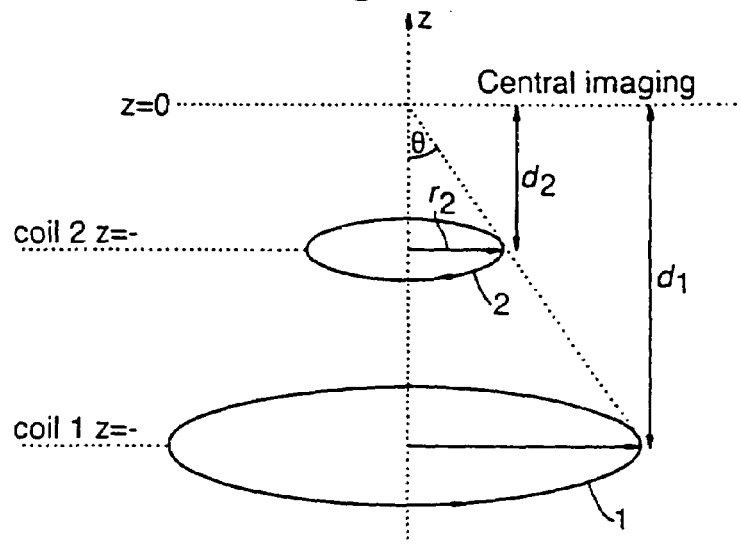
FIG. 7 shows a diagram of a pair of coils arranged to produce a longitudinal gradient.

We have found that it is possible to improve linearity and to eliminate the third order term if a second coil is introduced as shown in FIG. 7. From the condition in equation (24), the pair of coils will subtend the same angle at the central imaging plane, i.e. lie on a cone. This angle can be given as:

$$\theta = \tan^{-1}\frac{r_1}{d_1} = \tan^{-1}\frac{r_2}{d_2} \quad (25)$$

The field resulting from the double coil arrangement will be the sum of the fields generated by each coil. At z=0 it is found that the third order term can be made to vanish if:

$$\left(\frac{r_2}{r_1}\right)^4 = -\frac{I_2 N_2}{I_1 N_1} \quad (26)$$

The minus sign in the above condition indicates that the current should be flowing in the opposite direction in the second coil with respect to the direction of the current in the first coil. The two conditions at (24) and (26) can be used to eliminate the second and third order components of the Taylor expansion to give a linear magnetic field gradient which is linear up to fourth order.

Thus, a pair of substantially circular coils substantially satisfying equations (24) and (26) can project a highly linear gradient, up to fifth order in z.

Figure 8A:
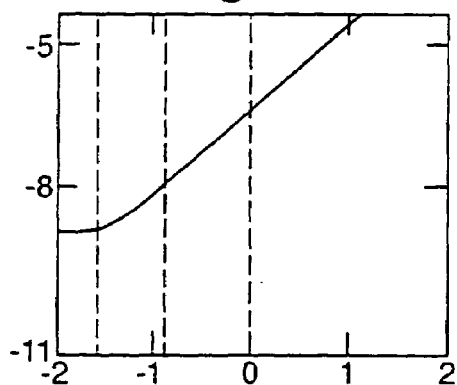
FIG. 8 show plots of the field and field gradient generated by a coil pair.
Figure 8B:
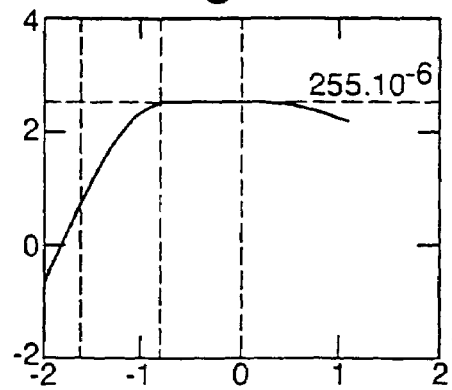
Figure 9:
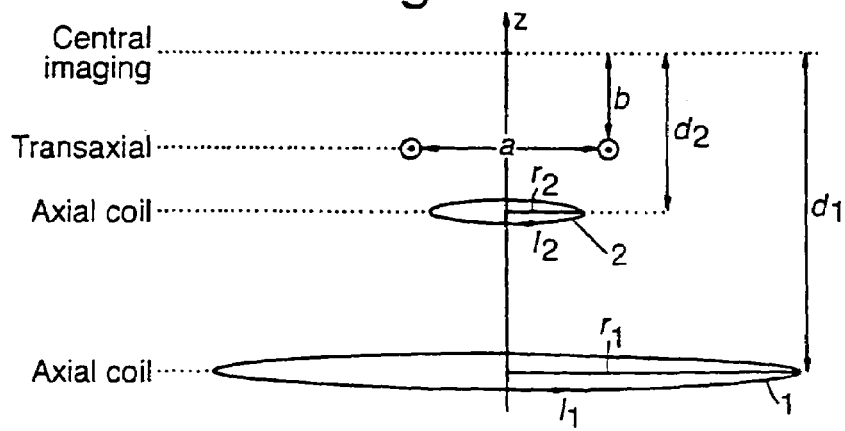
FIG. 9 shows a schematic diagram of the coils of FIG. 7.

FIG. 8 show plots of the field (FIG. 8a) and gradient (FIG. 8b) generated by a pair of coils satisfying the above conditions. Parameters are chosen to generate a field gradient of 2.5 Gauss $A^{-1}$ $cm^{-1}$.

As can be seen from FIG. 8a, since the central imaging plane is not the zero field plane, there will be a field offset in the z-direction (conventional arrangements can achieve a null field offset, but require coils either side of the sample). This means that the longitudinal gradient set should be used for slice or frequency encoding where it is possible to establish a compensatory frequency offset. This would not be the case for phase encoding where the amplitude of the applied gradient is not fixed during the imaging experiment.

The above arrangement can be used in place of the $G_z$ gradient coil of suitable apparatus.

Thus, using the arrangements described above, it is possible to project a substantially uniform linear magnetic field gradients in all three dimensions, based on relatively simple current elements and suitable for MRI.

Using the principles developed above, of adding elements to set higher order terms in the Taylor expansion (other approximations may be used) gradient linearity may be improved still further, if desired. It should also be possible to apply the principles outlined above to derive similar conditions for elements other than the wire pair and coil described above, and the invention is not to be construed as restricted to the above or following implementations. However, since the above arrangements can provide adequate linearity for most practical purposes and are relatively simple to implement a practical imaging system embodying the above principles will now be described in detail.

In the first version of the projection gradient design, two gradient systems were constructed one axial and one transaxial, allowing for frequency and phase encoding only. The target field gradient was 0.5 Gauss $A^{-1}$ $cm^{-1}$. In a later version, problems encountered in the first design were overcome and a third gradient was added to allow for slice selection. The target field gradient was also increased to 2.5 Gauss $A^{-1}$ $cm^{-1}$. A butterfly RF transmitter coil was built into the final gradient former design to provide remote excitation and detection of the nuclear spins, in keeping with the concept of a full projection system.

Conventional instrumentation was used to run the imaging experiments and will not be described in detail and to test the performance of the gradient sets. Although the magnet used was a conventional superconducting solenoid magnet, projection magnet designs to produce a remote $B_0$ field do exist and these would allow a complete projection MRI system to be constructed. (see U.S. Pat. No. 4,721,914)

Design and Construction of a Gradient Set.

A practical gradient set embodying the invention comprises two gradients systems: a longitudinal gradient system to generate a field gradient in the z direction, and a transverse gradient system to generate a field gradient in the x direction.

Practical Constructional Details—First Implementation

In a first implementation of this gradient set the target gradient was set to be 0.5 Gauss $A^{-1}$ $cm^{-1}$ for both gradient systems, corresponding to a 1 kHz profile basewidth for a 5 mm diameter NMR tube.

For the transverse gradient system, a pair of parallel wire bundles (4) in the transverse plane was used to generate the field gradient. According to equation (12), if b, the normal distance between the plane containing the pair of wire bundles and the central imaging plane is set to 5 mm, the value of a, the separation of wire bundles becomes 2d=1 mm. The error in the value of a results from the fact that the wires forming the bundles have a finite diameter of 0.5 mm. Setting the target field gradient in equation (13) to 0.5 Gauss $cm^{-1}A^{-1}$, requires N, the number of turns to be set to 3. Each bundle should therefore contain 3 wires.

For the longitudinal field gradient, substituting the condition of equation (26) for both coils into equation (24) and setting $dB_z/dz$ for the combination to 0.5 Gauss $cm^{-1}A^{-1}$, gives $$\frac{I_1 N_1}{a_1^4}(r_1^2 - r_2^2) = 9.268 \quad (27)$$

The upper, smaller coil (2) of the longitudinal gradient system, was chosen to lie immediately under the transverse gradient system with a distance ($d_2$) of 8 mm from the central imaging plane, see FIG. 7. According to equation (26), this requires $r_2$, the radius of the smaller coil, to be 16 mm. For the lower larger coil (1), the radius, $r_1$, was restricted by the shim set inner diameter (~73 mm) and was chosen to be 32 mm, giving a value for $d_1$ of 16 mm (equation (26)). Substituting the above values in equation (27) gives $N_1I_1=12.65$, and hence from equation (26) $N_2I_2=0.79$. The smaller upper coil was chosen to have a single turn ($N_2=1$) and the larger coil 13 turns ($N_1=13$). The current flowing in each coil must be manipulated to satisfy equation (28) and, therefore, a ratio of $I_2/I_1$ of 0.81 must be implemented.

Figure 10:
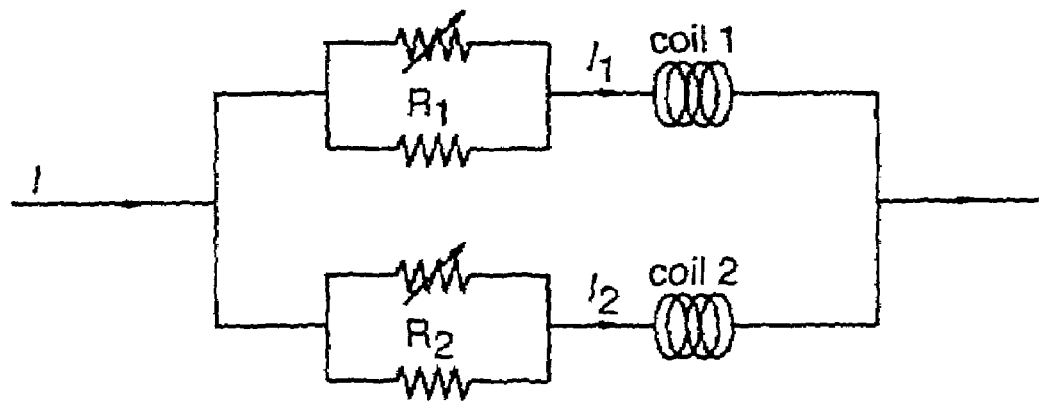
FIG. 10 shows a current divider circuit.

For this gradient set, a current divider circuit, shown in FIG. 10, was made so that one current source can supply both coils with the appropriate currents. The resistor values were chosen so that $R_2/R_1=0.81$ to provide the appropriate ratio of currents for the two coils.

Figure 11:
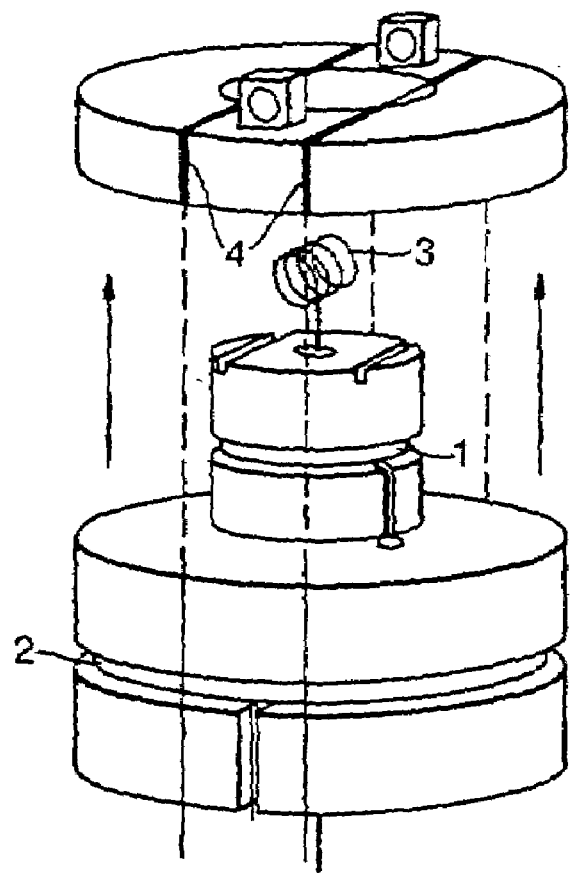
FIG. 11 shows a diagram of a probe head constructed for projection gradient imaging.

The wires forming the gradient coils were connected to a seven terminal socket fixed to the base of the probe. A four turn solenoid coil (3) with a diameter of 6 mm, positioned on the top of the gradient set, was used to transmit/receive the RF signals, as shown in FIG. 11. This coil was accurately centred with respect to the gradient set and connected to a set of capacitors to tune the coil to a specific frequency and match it to $50\Omega$.

The gradient coils were tested using a 5 mm diameter NMR tube filled with water. After inserting the probe into the magnet, tuning and matching were carried out to maximise the signal. For each gradient coil, the current was stepped in negative and positive values and the basewidths of the acquired profiles were measured. The transverse gradient was found to work well giving a gradient field value of 0.56 Gauss $A^{-1}$ cm$^{-1}$, agreeing, within experimental error, with values predicted theoretically.

Practical Constructional Details—Second Implementation

In a second implementation employing this construction, the target gradient was also increased to 2.5 Gauss cm$^{-1}$ A$^{-1}$. This was achieved by increasing the number of turns of the coils (for the longitudinal gradient system) and the number of wires in the bundles (for the transverse gradient system), whilst keeping all other dimensional constraints the same. A thinner wire, with a diameter of 0.315 mm instead of 0.5 mm, was used allowing the increased number of wires to be accommodated without excessively increasing the bundle thickness.

For the transverse system, achieving the increased gradient strength was straightforward since, from equation (9), to increase the field gradient by a factor of five the number of wires in both bundles needed to be multiplied by five. This would mean keeping all other parameters on the system the same but having fifteen turns for each bundle rather than the three that were used in the old set.

To achieve an increased gradient strength for the longitudinal system, the gradient in equation (22) for the coil combination was set to 2.5 Gauss cm$^{-1}$ A$^{-1}$. The conditions in equation (28) were set so that $I_1=I_2$ to avoid using the current divider circuit, and $N_1$ and $N_2$ were manipulated so that the number of turns in each coil was as close to a whole number as possible. $N_1$ was set to be 63 and $N_2$ to 4, and the dimensions and positions of the coils were the same as before. Another former with increased depth and width of the wire channels to accommodate the larger number of wires is required. All wires are fixed into their respective channels and glued at regular intervals to prevent any loosening during winding and finally covered with epoxy resin to avoid any short circuiting of the coils and to protect the outer wires.

A number of experiments were carried out with the second implementation to compare the measured gradient field with theoretical predictions, and to test the gradient linearity and eddy current effects.

Experimental Results

1) Gradient Field Strength Test.

The gradient coils were tested using a 2.3 mm internal diameter capillary tube filled with water. For each gradient system, the current was stepped through negative and positive values and the basewidth of the acquired profile was measured.

The symmetry of the profile basewidth about I=0 was greatly improved. The following table lists some of the gradient parameters obtained for the gradient system.

| Gradient Direction | Gradient Efficiency (Gauss A$^{-1}$cm$^{-1}$) | (kHz A$^{-1}$cm$^{-1}$) | Resistance ($\Omega$) | Inductance ($\mu$H) |
|---|---|---|---|---|
| Longitudinal | | | | |
| z-Gradient | | | | |
| Small coil | 0.6 ± 0.03 | 2.587 | 0.39 | 2.6 |
| Large coil | 3.19 ± 0.06 | 13.586 | 3.02 | 525 |
| Combination ($I_1 = -I_2$) | 2.54 ± 0.04 | 10.856 | 3.41 | 517 |
| Transverse | | | | |
| x-Gradient | 2.36 ± 0.05 | 10.048 | 2.20 | 120.8 |

The results indicate good agreement with the theoretically predicted values. The longitudinal gradient coil combination gave a value of 2.54±0.04 Gauss A$^{-1}$ cm$^{-1}$ very close to the theoretically predicted value of 2.5 Gauss A$^{-1}$ cm$^{-1}$.

For the transverse system, a gradient value of 2.36±0.05 Gauss A$^{-1}$ cm$^{-1}$ was obtained. The small difference from the theoretical value probably originates from the fact that the theoretical calculations were based upon a pair of infinitely long wires with negligible cross section, which clearly is not the case in this design.

The new version of the transverse gradient system also showed an improvement in the gradient field offset of the profile midpoint with increasing current. The actual shift was reduced from ~3000 Hz A$^{-1}$ in the transverse system of the old set to only ~700 Hz A$^{-1}$ in the new one. This corresponds to a marked improvement of the centralisation of both the sample and the RF coil.

2) Gradient Field Linearity Assessment.

The linearity of the magnetic field gradients produced by the system is very important since it determines the spatial fidelity of the final image.

Figure 12:
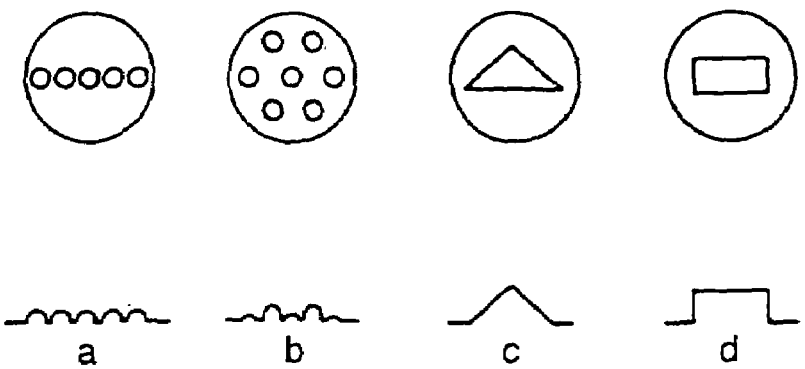
FIG. 12 show diagrams of a number of phantoms used in experiments.

A number of simple experiments were carried out to test the linearity using a variety of differently shaped phantoms, shown in FIG. 12. The NMR profile of each was measured and compared with the actual dimensions of the phantom.

The phantom shown in FIG. 12a consisted of 5 holes each of diameter 0.38 mm with 0.66 mm separation between centres of adjacent holes. The phantom was filled with water using a thin piece of wire to remove the air from the holes. The phantom was then placed in the RF solenoid coil ensuring that the long axis of the holes was aligned parallel to the allocated read gradient. One-dimensional profiles were obtained from the phantom using the transverse and longitudinal gradient systems in turn.

Figure 13A:
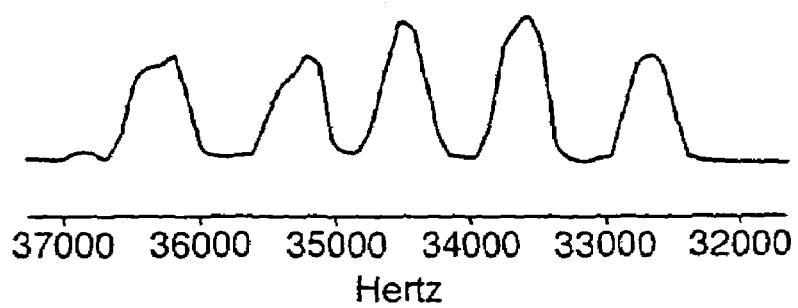
Figure 13B:
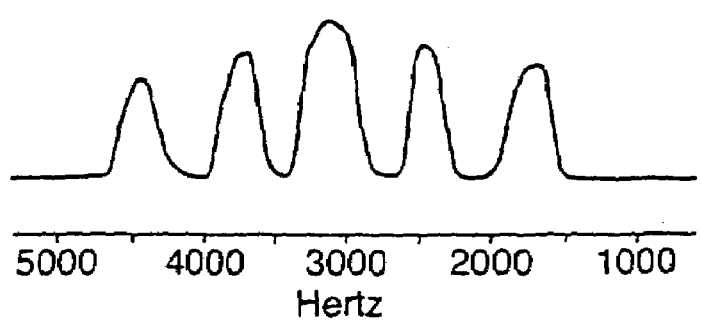

For all the profiles obtained for both the transverse and the longitudinal systems, variation in the peak heights of the semiellipses along the array were observed, indicating a difference in the amount of water in each hole, as shown in FIGS. 13a and 13b. Because of the small size of the holes it was very difficult to ensure that the five holes contained the same amount of water. Furthermore, shimming was extremely difficult since the acquired signal was very small and there were adverse susceptibility effects due to edges; these factors were reflected in the shape of the profiles.

However, when basewidth values were taken from both systems and converted from frequency to spatial dimensions (using the average gradient values obtained for the corresponding gradient, from the table above), the corresponding phantom dimensions were found to be from 20 to 25% less than the true values. This difference is believed to be partly due to an error in the dimensions of the holes and due to susceptibility effects at the margins. Nevertheless, profiles indicated good linearity over the sample, with good profile shape and approximately equal separation between the semiellipses.

3) Eddy Current Test.

The rapidly changing magnetic fields arising from pulsed gradient fields interact with surrounding metal and induce eddy currents in it. In NMR imaging experiments this can severely degrade the image quality.

One advantage of using an open system for NMR imaging is the possibility of virtually excluding eddy current effects. However, in the testing procedure, the gradient system was tested with a closed superconducting magnet with a metallic bore which is highly susceptible to eddy currents. A few simple experiments were carried out to investigate their effect on the signal. The gradient pulse was switched on for a short time, after which a variable delay (D4) was left to allow the eddy currents to subside. Finally a 90° excitation pulse was applied and the signal acquired.

Imaging using the Projection Gradient Coils.

Figure 14:
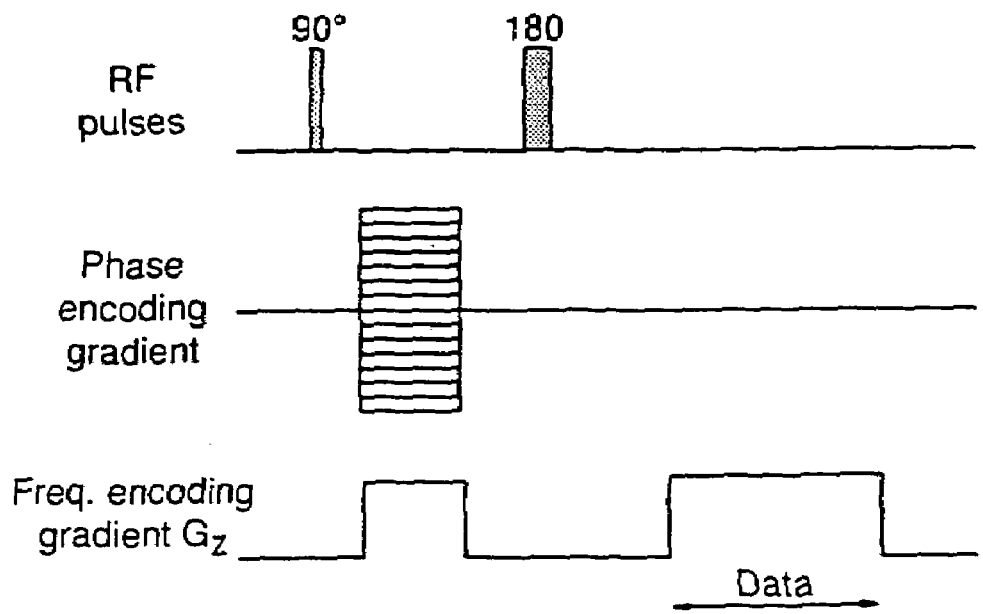
FIG. 14 shows a timing diagram of a pulse sequence used in a 2D imaging experiment.

Initially, simple 2D imaging experiments based on the spin echo pulse sequence were carried out to test the suitability of the new projection gradient system for imaging. The timing diagram for the pulse sequence used in the imaging experiments is shown in FIG. 14. As the original gradient set consisted of only a two gradient system, the imaging experiments were carried out without slice selection.

Images were acquired with a matrix size of either 128×64 or 128×128 pixels. The longitudinal gradient set was used for frequency encoding because of the frequency offset changes with applied current which precluded its use for phase encoding. A compensation frequency offset was established by calibration measurements taken for different current values. A one dimensional profile for the object was first produced by setting the phase encoding gradient to zero, then 64 or 128 phase encoding steps were run to produce a 2D image. A conventional gradient pulse programmer unit was used to generate the gradient pulses and multiply the phase encoding values to give the desired image matrix.

Figure 15A:
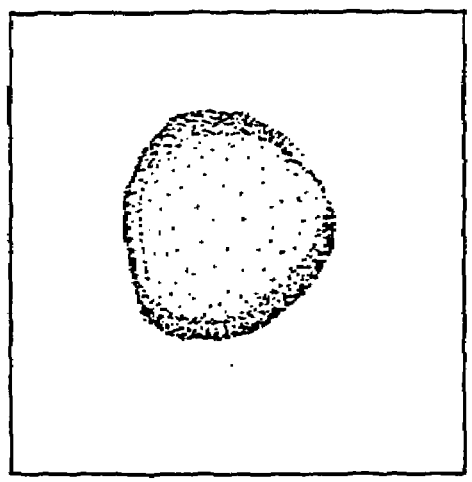
FIG. 15 show images of a tube filled with water, and the former shown in FIG. 12b, obtained using projection gradient coils.
Figure 15B:
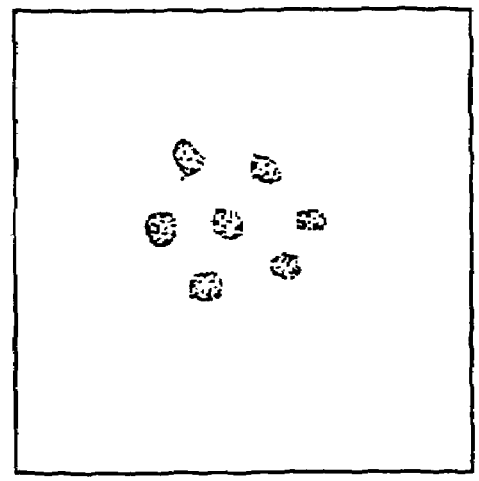

FIG. 15 show 128×128 images for a 2.3 mm diameter tube filled with water (FIG. 15a) and for the former shown in FIG. 12b (FIG. 15b). A variation in the strength of the transverse gradient field was noticed particularly in planes above the central imaging plane, as can be seen in FIG. 15. As described in the theory above, this problem can be eliminated by introducing another double pair of coils below the first one to reduce significantly the z-dependence of the transverse gradient. This should correct the field gradient linearity to third order.

Although embodiments have been described using one or two coils, three or more coils could be used in order to generate higher gradients. For example, a plurality of coils could be located along a conical former, and the density of the coil windings adjusted to achieve the required field.

A Complete Projection Probe for NMR Imaging.

Figure 17:
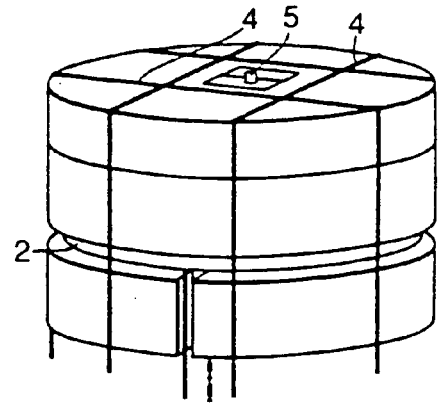
FIG. 17 shows a diagram of a projection probe head with a butterfly coil.

Referring to FIG. 17, a complete projection imaging probe can be constructed from the second implementation by the addition of a transverse gradient system at 90° with respect to the original transverse system. This new gradient system can be sited just above the original transverse system, 4 mm from the central imaging plane, with the separation between the new bundles set accordingly to 20 mm. This completes the field gradients required for MRI spatial encoding in three dimensions.

Figure 16:
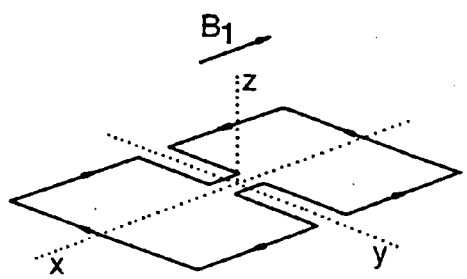
FIG. 16 shows a butterfly shaped coil and a diagram of its electric circuit.
Figure 16:
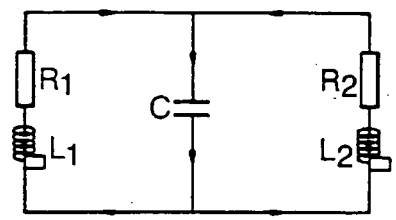

The projection probe is advantageously completed by the addition of a planar pair or butterfly coil (5) as an RF transmit/receiver coil. Introducing the butterfly coil which generates a $B_1$ field parallel to its plane allows it to be mounted on the surface of the flat gradient system. The butterfly coil is built from two flat loops of wire lying in the same plane, and connected in parallel. The coil is shown schematically in FIG. 16.

A 1×1 cm butterfly coil was mounted on the top of the gradient assembly in such a way that the central image plane for the three gradient sets matches the centre of the homogenous area of the butterfly coil. A schematic diagram of locations of the gradient coils with respect to the RF butterfly coil is shown in FIG. 17.

The efficiency of the y-gradient of such a system has been determined by measuring the profile basewidth of a 5 mm diameter NMR tube filled with water for a number of negative and positive current values. The additional transverse system gives a gradient value of 11.284 kHz $A^{-1}$ $cm^{-1}$, corresponding to 2.65±0.08 Gauss $A^{-1}$ $cm^{-1}$ compared with the theoretically predicted value of 2.5 Gauss $A^{-1}$ $cm^{-1}$. The resistance and inductance of this gradient coil were 2.4Ω and 138.6 µH respectively. The probable reason for the slight discrepancy in the y-gradient efficiency is the same as that suggested for the x-gradient, namely that the theoretical values were based upon a pair of infinitely long wires of negligible cross section.

Imaging with the Complete System.

A 2D spin-warp imaging experiment, with slice selection, was carried out using the three gradient system. The sample was carefully mounted on the top of the butterfly coil so as to occupy the linear part of the gradient system. An image was taken in the x-y plane (parallel to the RF coil). The transverse gradient sets were used as phase and frequency encoding gradients and the longitudinal gradient was used as the slice selection gradient. In this way the problem originating from the z-dependence of the transverse gradient in the simple uncorrected design was avoided.

Figure 18A:
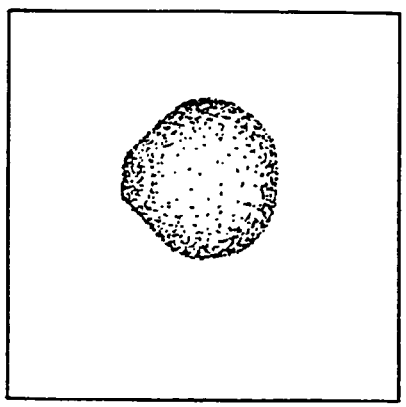
FIG. 18 show images of a bulb of water obtained with the projection probe of FIG. 17.
Figure 18B:
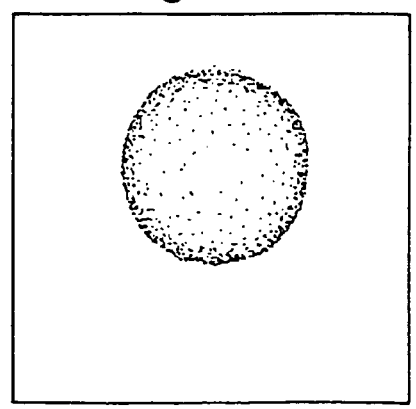

FIG. 18 show images taken using the complete projection probe. The first image is a cross sectional slice through a 4 mm diameter bulb filled with water and the second image is a similar cross section through a 5 mm diameter NMR tube filled with water. The images show good symmetry when compared with those of FIG. 15.

Thus it can be seen that even relatively simple practical implementations of a gradient set showed results in good agreement with the theoretical predictions, enabling production of slice selected images for various samples using a complete projection imaging probe.

The arrangements described can be used for generating a remote gradient system to be used for MRI in medical and industrial applications. The apparatus described can readily be scaled to provide larger systems. In conjunction with a suitable open magnet system of the type described, "flat-bed" systems for imaging of objects such as a patient or an animal or an industrial object are therefore possible, allowing an entire hemisphere of access to the sample, while imaging is in progress.

What is claimed is:

1. Magnetic gradient field projection apparatus for generating a magnetic field along a projection axis, in a defined sample volume offset from and outside said apparatus, said projection apparatus comprising:

gradient field generating means arranged to generate a substantially linear axial gradient component in said sample volume, said gradient field generating means comprising a substantially circular first coil positioned so that the center of the first coil is displaced along the axis of the first coil away from the centre of the sample volume by a distance approximately equal to half of the radius $r_1$ of the first coil, such that the second derivative of the axial gradient component is substantially equal to zero at the center of the sample volume, a further coil, the axis of the first coil being substantially coincident with the axis of said first coil, and distance of said further coil from the center of the sample volume, and the radius of the further coil, being selected such the angle subtended at the center of the sample volume by each of said first and further coils is substantially the same;

the distance of said further coil from the center of the sample volume being substantially equal to half of the radius $r_2$ of the further coil, the first and further coils being connected so that, in use, the relation $$\left(\frac{r_2}{r_1}\right)^4 = -\frac{I_2 N_2}{I_1 N_1}$$

is substantially satisfied where $I_1$ and $I_2$ are the currents flowing through said first coil and said further coil respectively, and $N_1$ and $N_2$ are the numbers of turns of said first coil and said further coil respectively, the radii of the first and further coils being mutually different, the currents in the first and further coils flowing in opposite directions.

2. Apparatus according to claim 1 comprising a plurality of substantially circular coils of differing radii arranged in substantially parallel planes with their centers passing through a common axis, the distance of each coil from the center of the sample volume, and the radius of each coil, being selected such the angle subtended at the center of the sample volume by each of said coils is substantially the same.

3. Magnetic gradient field projection apparatus for generating a magnetic field along a projection axis, in a defined sample volume offset from and outside said apparatus, comprising gradient field-generating means arranged to generate, in use, a transverse gradient component of said magnetic field which is substantially linear within said defined sample volume, said gradient field-generating means comprising:

two substantially parallel long substantially straight conductors substantially symmetrically located about an axis passing through the center of the sample volume, said conductors lying in a plane substantially perpendicular to the projection axis and offset along said projection axis from the center of the sample volume, wherein the conductors are arranged to carry substantially equal currents in a common direction and are positioned relative to the center of the sample volume such that the second derivative of the transverse gradient component in the transverse direction is substantially equal to zero at the center of the sample volume.

4. Apparatus according to claim 3, wherein the spacing $a_1$ between the conductors and the distance $d_1$ of the plane through the conductors from the center of the sample volume, substantially satisfy the relation $a_1^2 = 4d_1^2(3 +/- 2\sqrt{2})$.

5. Apparatus according to claim 4, wherein:

a further pair of substantially parallel conductors is provided, the plane of the further pair being substantially parallel to the plane of said pair of conductors, the current in the further pair arranged to flow in the opposite direction to the current in said pair of wires, the distance of the further pair being greater than the distance of said pair of wires, the separation $a_2$ of the further pair of conductors or wire bundles and the distance $d_2$ of the further pair of conductors or wire bundles from the sample plane substantially satisfying the relation $a_2^2 = 4d_2^2(3 +/- 2\sqrt{2})$, and the currents in the conductors or wire bundles further substantially satisfying the relation $\Sigma I_2/\Sigma I_1 = (a_2/a_1)^3$, where $\Sigma I_1$, $\Sigma I_2$ are the total currents in each conductor for the first and second pairs respectively.

6. Apparatus according to claim 4, wherein:

a further pair of substantially parallel conductors is provided, the plane of the further pair being substantially parallel to the plane of said pair of conductors, the current in the further pair arranged to flow in the opposite direction to the current in said pair of wires, the distance of the further pair being greater than the distance of said pair of wires, the separation $a_2$ of the further pair of conductors or wire bundles and the distance $d_2$ of the further pair of conductors or wire bundles from the sample plane substantially satisfying the relation $a_2^2 = 4d_2^2(3 +/- 2\sqrt{2})$, and the currents in the conductors or wire bundles further substantially satisfying the relation $\Sigma I_2/\Sigma I_1 = (a_2/a_1)^6$, where $\Sigma I_1$, $\Sigma I_2$ are the total currents in each conductor for the first and second pairs respectively.

7. A magnetic field projection apparatus comprising a plurality of gradient field generating elements arranged to generate substantially linear magnetic gradient field components in mutually orthogonal directions in a sample volume offset from and outside said apparatus, wherein said magnetic field generating elements comprise:

an axial gradient component generating element comprising a substantially circular coil positioned so that the center of the coil is displaced along the axis of the coil away from the center of the sample volume by a distance approximately equal to half of the radius $r_1$ of the coil, such that the second derivative of the axial gradient component is substantially equal to zero at the center of the sample volume; and, a transverse gradient component generating element, comprising two substantially parallel long substantially straight conductors substantially symmetrically located about an axis passing through the center of the sample volume, said conductors lying in a plane substantially perpendicular to the projection axis and offset along said projection axis from the center of the sample volume, wherein the conductors are arranged to carry substantially equal currents in a common direction and are positioned relative to the center of the sample volume such that the second derivative of the transverse gradient component in the transverse direction is substantially equal to zero at the center of the sample volume.

8. Apparatus according to claim 1 further including:
a housing,
means for defining a sample volume outside the housing;
a magnet assembly within the housing for generating a static magnetic field within the defined sample volume along the projection axis;
a radio frequency transceiver within the housing for transmitting signals to and receiving signals from the defined sample volume; and
control apparatus for controlling said magnetic field generating elements to generate said at least one gradient component in conformity with an imaging protocol.

9. Apparatus according to claim 8, wherein said means for defining the sample volume comprises an operating surface to the outside of said housing over which a sample to be imaged, preferably a patient, can be positioned.

10. Apparatus according to claim 1 further comprising:
means for applying current to generate desired gradient components in accordance with a given imaging protocol.

11. Magnetic resonance spectroscopy system comprising an apparatus according to claim 1.

12. A method of configuring a magnetic gradient field projection apparatus according to claim 1 to produce a substantially linear magnetic field gradient component within the defined sample volume, said method comprising:
positioning the gradient field generating means with respect to the sample volume so that the second derivative of a desired component of the magnetic field with respect to distance along a predetermined direction corresponding to said magnetic field gradient component is substantially equal to zero at least about a predetermined point within the defined sample volume at the proximity of the center of the sample volume.

13. A method according to claim 12, further comprising:
arranging the assembly so that the third derivative of said component of the magnetic field with respect to distance along said predetermined direction is substantially equal to zero at least about said predetermined point within the defined sample volume.

14. A method for generating a magnetic field along a projection axis, in a defined sample volume offset from and outside apparatus for generating a gradient field so as to generate a substantially linear axial gradient component in said sample volume, said gradient field generating method comprising:
positioning substantially circular first coil so that the center of the first coil is displaced along the axis of the first coil away from the center of the sample volume by a distance approximately equal to half of the radius $r_1$ of the first coil, such that the second derivative of the axial gradient component is substantially equal to zero at the center of the sample volume,
providing a further coil, the axis of the first coil being substantially coincident with the axis of said first coil, and distance of said further coil from the center of the sample volume, and the radius of the further coil, being selected such the angle subtended at the center of the sample volume by each of first and further coils is substantially the same;
the distance of said further coil from the center of the sample volume being substantially equal to half of the radius $r_2$ of the further coil, the first and further coils being connected so that, in use, the relation $$\left(\frac{r_2}{r_1}\right)^4 = -\frac{I_2 N_2}{I_1 N_1}$$

is substantially satisfied where $I_1$ and $I_2$ are the currents flowing through said first coil and said further coil respectively, and $N_1$ and $N_2$ are the numbers of turns of said first coil and said further coil respectively, the radii of the first and further coils being mutually different, the currents in the first and further coils flowing in opposite directions.

15. A method as in claim 14 comprising arranging a plurality of substantially circular coils of differing radii arranged in substantially parallel planes with their centers passing through a common axis, the distance of each coil from the center of the sample volume, and the radius of each coil, being selected such the angle subtended at the center of the same volume by each of said coils is substantially the same.

16. A method for generating a magnetic field along a projection axis, in a defined sample volume offset from and outside gradient field-generating apparatus arranged to generate, in use, a transverse gradient component of said magnetic field which is substantially linear within said defined sample volume, said gradient field-generating method comprising:
positioning two substantially parallel long substantially straight conductors substantially symmetrically about an axis passing through the center of the sample volume,
said conductors lying in a plane substantially perpendicular to the projection axis and offset along said projection axis from the center of the sample volume,
wherein the conductors are arranged to carry substantially equal currents in a common direction and are positioned relative to the center of the sample volume such that the second derivative of the transverse gradient component in the transverse direction is substantially equal to zero at the center of the sample volume.

17. A method as in claim 16 wherein the spacing $a_1$ between the conductors and the distance $d_1$ of the place through the conductors from the center of the sample volume, substantially satisfy the relation $a_1^2 = 4d_1^2(3+/-2\sqrt{2})$.

18. A method as in claim 17 wherein a further pair of substantially parallel conductors is parallel such that:
the plane of the further pair being substantially parallel to the plane of said pair of conductors,
the current in the further pair arranged to flow in the opposite direction to the current in said pair of wires,
the distance of the further pair being greater than the distance of said pair of wires,
the separation $a_2$ of the further pair of conductors or wire bundles and the distance $d_2$ of the further pair of conductors or wire bundles from the sample plane substantially satisfying the relation $a_2^2 = 4d_2^2(3+/-2\sqrt{2})$, and
the currents in the conductors or wire bundles further substantially satisfying the relation $\Sigma I_2/\Sigma I_1 = (a_2/a_1)^3$, where $\Sigma I_1$, $\Sigma I_2$ are the total currents in each conductor for the first and second pairs respectively.

19. A method as in claim 17 wherein a further pair of substantially parallel conductors is provided such that:

the plane of the further pair being substantially parallel to the planes of said pair of conductors, the current in the further pair arranged to flow in the opposite direction to the current in said pair of wires, the distance of the further pair being greater than the distance of said pair of wires, the separation $a_2$ of the further pair of conductors or wire bundles and the distance $d_2$ of the further pair of conductors or wire bundles from the sample plane substantially satisfying the relation $a_2^2 = 4d_2^2(3+/-2\sqrt{2})$, and the currents in the conductors or wire bundles further substantially satisfying the relation $\Sigma I_2/\Sigma I_1 = (a_2/a_1)^6$, where $\Sigma I_1$, $\Sigma I_2$ are the total currents in each conductor for the first and second pairs respectively.

20. A method for projecting a magnetic filed comprising:

arranging a plurality of gradient field generating elements to generate substantially linear magnetic gradient field components in mutually orthogonal directions in a sample volume offset from and outside the field generating apparatus, wherein said magnetic field generating elements comprising:

an axial gradient component generating element comprising a substantially circular coil positioned so that the center of the coil is displaced along the axis of the coil away from the center of the sample volume by a distance approximately equal to half of the radius $r_1$ of the coil, such that the second derivative of the axial gradient component is substantially equal to zero at the center of the sample volume; and a transverse gradient component generating element, comprising two substantially parallel long substantially straight conductors substantially symmetrically located about an axis passing through the center of the sample volume, said conductors lying in a plane substantially perpendicular to the projection axis and offset along said projection axis form the center of the sample volume, wherein the conductors are arranged to carry substantially equal currents in a common direction and are positioned relative to the center of the sample volume such that the second derivative of the transverse gradient component in the transverse direction is substantially equal to zero at the center of the sample volume.

* * * * *